United States Patent [19]
Antonelli et al.

[11] 3,962,286
[45] June 8, 1976

[54] CATALYTIC PROCESS FOR PREPARING ETHYLENE OXIDE BY OXIDATION OF ETHYLENE

[75] Inventors: Giambattista Antonelli, Brugherio (Milan); Natale Ferlazzo, Segrate (Milan); Giancarlo Aglietti, Milan, all of Italy

[73] Assignee: Societa' Italiana Resine S.I.R. S.p.A., Milan, Italy

[22] Filed: Dec. 17, 1974

[21] Appl. No.: 533,603

[30] Foreign Application Priority Data
Dec. 28, 1973 Italy.................................. 32343/73

[52] U.S. Cl............................................ 260/348.5 R
[51] Int. Cl.²........................................ C07D 301/10
[58] Field of Search.............................. 260/348.5 R

[56] References Cited
UNITED STATES PATENTS 2,831,870   4/1958   McClements et al........ 260/348.5 R
3,663,455   5/1972   Calcagno et al.................... 252/443

Primary Examiner—Norma S. Milestone
Attorney, Agent, or Firm—Sughrue, Rothwell, Mion, Zinn & Macpeak

[57] ABSTRACT

Ethylene oxide is prepared by oxidation of ethylene on a catalyst obtained by:
  a. impregnating particles of a subdivided inert support with a decomposable silver salt,
  b. drying said impregnated particles by heating to a maximum temperature not exceeding 160°C,
  c. flowing through the dried particles a gaseous stream of superheated steam, the temperature being raised to a selected value from 270° to 350°C,
  d. gradually replacing the steam by air over a period of at least 1 hour with the temperature being maintained at said selected value, and
  e. maintaining the particles for at least 30 minutes under the stream of air, with the temperature being maintained at said selected value.

17 Claims, No Drawings

3,962,286

CATALYTIC PROCESS FOR PREPARING ETHYLENE OXIDE BY OXIDATION OF ETHYLENE

BACKGROUND OF THE INVENTION

1. Field of the Invention

The invention relates to an improvement in the process of preparing ethylene oxide by oxidation of ethylene with gaseous oxygen on a silver-based catalyst.

More particularly, the invention relates to the use of a silver-based supported catalyst, active in the oxidation process, and obtained by impregnation of a granular inert support with a decomposable silver salt, followed by drying and decomposition of the silver salt on the support, with the decomposition being carried out under specific conditions.

2. Description of the Prior Art

According to a process employed in the art, to a great extent ethylene oxide is obtained by contacting at high temperature ethylene with gaseous oxygen on a silver-based catalyst.

This catalyst usually consists of a granular inert support on which silver and possibly also minor quantities of additional metals such as platinum, gold, palladium, barium and calcium are deposited.

According to the process known in the art, the silver-based catalysts are prepared by impregnation of a subdivided inert support with a decomposable silver salt. Silver lactate is particularly suitable and can be used either a molten condition or a dissolved condition. The impregnated support is then dried and subsequently heat-treated at high temperature whereby the silver salt is decomposed by heat and metallic silver is fixed on the support.

The thermal decomposition (or activation of the catalyst) is normally carried out at a temperature from 250° to 400°C in an oxidizing atmosphere such as in the presence of air, or initially in a nitrogen atmosphere, and then in a nitrogen-oxygen atmosphere with a progressively increasing oxygen proportion.

According to another process known in the art, activation of the catalyst is still effected in a nitrogen-oxygen atmosphere with an increasing oxygen proportion, with the gases evolved on decomposition of the silver salt being caused to continuously flow through the catalyst particles. In this manner an influence is exerted up to a certain extent on the nature of the silver deposit on the support and, ultimately, on the properties of the catalyst.

According to what is known in the art, the nature of the silver deposit obtained from the decomposable salt and the adherence of the silver to the support are rather largely influenced by the carbon dioxide present in the gaseous atmosphere in contact with the catalyst being formed.

Therefore, according to a further known process, the decomposition of the silver salt is carried out in an oxidizing atmosphere which contains substantial quantities of carbon dioxide.

Further processes are moreover known for preparing active silver-based catalysts, with an activation step being carried out at high temperature in a non-oxidizing atmosphere or in a reducing atmosphere.

SUMMARY OF THE INVENTION

It has now been found that the use of superheated steam in the catalyst activation step and under the conditions described hereafter affords an accelerated activation of the catalyst and confers to the catalyst valuable properties, more particularly valuable mechanical properties.

Moreover, by operating according to the present invention, the control of the temperature at the decomposition step of the silver salt is facilitated. Control of temperature within narrow limits is a necessary condition for correct activation.

An object of the invention is to provide a process for preparing ethylene oxide, comprising the step of contacting a gaseous stream containing ethylene and oxygen with a silver-based catalyst of improved properties.

Thus, the invention provides a process for preparing ethylene oxide by catalytic oxidation of ethylene with oxygen, which comprises reacting ethylene and molecular oxygen on a catalyst obtained by the following steps:

a. impregnating particles of a subdivided inert support with a heat-decomposable silver salt, b. drying the impregnated particles while heating to a maximum temperature not exceeding 160°C, c. flowing a gaseous stream consisting of superheated steam through the dried particles, while raising the temperature to a selected value in the range from 270° to 350°C, d. progressively replacing in the gaseous stream the superheated steam by air value, a period of at least 1 hour while maintaining the temperature at a value substantially equal to the selected value, and e. maintaining the catalyst for at least 30 minutes under the gaseous stream consisting of air, with the temperature being still maintained at a value substantially equal to the said selected value.

DETAILED DESCRIPTION OF THE INVENTION

The decomposable silver salts useful for the purpose of the invention are preferably the salts of lactic, citric, malic and isomalic acids, among which silver lactate is preferred.

The support is chosen from those conventionally employed in the art, such as alumina, silicon carbide, magnesium oxide and mixtures thereof. Alpha-alumina activated by treatment at a temperature over 1000°C and having a specific surface area of from 0.01 to 1.0 sq.m/g, a porosity of 10–50% and an average pore diameter of 20 to 180 microns is particularly useful.

The support is advantageously employed in the form of beads 4 to 9 mm in diameter.

According to the process of the present invention the support is first impregnated in a known manner with a decomposable silver salt. Thus, for instance, molten silver lactate or a solution of silver lactate in lactic acid or aqueous lactic acid can be employed. In the latter case, the lactic acid is usually present in a molar excess of 20 to 200%.

Impregnation is conveniently carried out at a temperature from 60° to 115°C and with a quantity of the sliver salt so as to provide a proportion of silver metal of 7 to 30% by weight with respect to the support in the finished catalyst.

Moreover, during the impregnation step, promoters for the oxidation reaction of ethylene can be added, such as palladium, gold or platinum, typically in a proportion of 0.01 to 1.0% by weight with respect to silver metal.

These promoters can be added in their metallic form as such or the products known in the trade as palladiated carbon, platinated carbon or carbon impregnated with colloidal platinum can be employed. These materials are preferably employed in the form of granules of a size of 0.1 to 100 microns.

The metallic promoters or the palladiated and platinated carbon or the carbon impregnated with colloidal platinum may be suspended in the solution of the decomposable silver salt and the support may be impregnated with the resulting suspension.

Further promoters, such as barium and calcium, can be added to the solution of the silver salt, for example in the form of a salt of the lactic acid and in a quantity of from 0.1 to 5 atoms of barium or calcium to 100 atoms of silver.

Impregnation of the particles of the support can be conveniently carried out in equipment comprising a rotary evaporator. The impregnated particles are subsequently dried. To this end the particles are conveniently caused to roll in an air stream, at a temperature progressively increasing to a maximum value not exceeding 160°C, for a period of from 1 to 10 hours.

In step (c), the stream of steam is advantageously conveyed through the particulate material at a velocity in the range from 0.1 to 5 meters/second, preferably of the order of 0.5 meters/second. In this manner the temperature of the material is controlled very closely.

During step (d), air progressively replaces the steam over a period of not less than 1 hour, preferably over a period of not less than 2 hours. The maximum period for replacing steam by air is not critical and can be even up to 50 hours.

During step (d), the velocity of the gaseous stream flowing through the particulate material is conveniently maintained within the range indicated for step (c).

When the steam has been fully replaced by air, the air flow is continued for at least 30 minutes. In this case also, the maximum period is not critical and the best results are obtained with flow periods of the order of 1–2 hours. During the treatment with air the velocity of the gaseous stream is conveniently maintained within the range indicated for step (c). Though any temperature within the range from 270° to 350°C can be employed in steps (c), (d) and (e), best results are obtained with a value selected in the range from 290° to 320°C.

In an embodiment of the process of the invention the impregnated and dried particles for the catalyst are charged to a vessel, generally of a vertically elongated tubular form, at the top of which the previously described gaseous stream is supplied.

The gases issuing at the bottom of the vessel are discharged as preferably no recycle is effected. By operating in the described manner, the temperature is easily controlled during activation of the catalyst and can be maintained with a precision of ±5°C, preferably ±2°C, with respect to the selected value.

It was moreover found that the use of steam results in a deposit of metallic silver on the support in the form of extraordinarily uniform fine grains. The resulting catalyst has valuable mechanical properties and can be used over prolonged periods of time in industrial processes for preparing ethylene oxide. The valuable properties of activity and selectivity of the catalyst in the above-mentioned process are maintained at a high level over the course of time.

Moreover, the catalyst preparation step in which the silver salt is decomposed is considerably simplified. More particularly, a peculiarity of the process is the possibility of obtaining an accelerated activation of the catalyst, whereas it was believed that prolonged activation periods were necessary in order to confer satisfactory properties to the catalyst. The catalyst is employed in the process of the invention for preparing ethylene oxide by oxidation of ethylene with oxygen at high temperature.

More particularly, in this process, a gaseous stream containing ethylene and oxygen is supplied to the catalyst and the process is generally carried out at a temperature from 200° to 330°C, at a pressure from 1 to 30 atm and for a contact period from 1 to 10 seconds.

The following experimental examples will further illustrate the invention.

EXAMPLE 1

37.5 g of lactic acid are admixed with 25.5 g silver oxide, 2.4 g of hydrogen peroxide and 0.7 g of barium hydroxide having 8 molecules of water of crystallization in the molecule.

The resulting solution is used to impregnate 150 g of beads of macroporous alpha-alumina, 8 mm in diameter, heated to 80°C. The alpha-alumina had been previously activated by treatment at a temperature above 1,000°C and had the properties hereinbefore-described. The beads are then caused to roll under a flow of 50 N liters/hour of air and the temperature is raised to 120°C in 7 hours.

The dried beads are placed in a tubular reactor, at the top of which superheated steam is fed at a velocity of about 0.6 meter/second and at a rate of about 75 N liters/hour, at atmospheric pressure until a temperature of 300°C is reached. Admission of air is then started in a progressively increasing proportion until the steam is fully replaced over a period of 6 hours. During this period, the feed rate of the gaseous stream is constantly maintained at about 75 N liters/hour with, the temperature being maintained around 300°C. Flow of air is then continued through the bed of particles for 2 hours with, the air rate and the temperature being maintained at the previously defined values. Finally, cooling is effected and the catalyst is discharged.

EXAMPLE 2

The solution of silver lactate in lactic acid described in Example 1 is admixed with 3.1 g of platinated carbon containing 5% by weight platinum. The resulting suspension is used to impregnate 300 g of beads of macroporous alpha-alumina (similar to that described in Example 1) heated to 80°C. The beads are then caused to roll under a flow of air supplied at a rate of 50 N liters/hours, the temperature being progressively raised to 160°C in 4 hours.

The dried beads are charged to a tubular reactor through which superheated steam is caused to flow at a velocity of 1.2 meters/second and at a rate of 300 N liters/hour, at atmospheric pressure until the temperature of the beads reached 300°C.

Admission of air is then started in a progressively increasing manner so as to fully replace the steam in a period of 6 hours. Flow of air is then continued for 2 hours.

During treatment with the steam-air mixture and air alone the temperature is maintained at around 300°C and the rate of gaseous flow at about 300 N liters/hour. Finally, cooling is effected and the catalyst is discharged.

EXAMPLE 3

36 g catalyst prepared as described in Example 1 are charged to a tubular reactor of AISI 316 steel, 9 mm in bore. A gaseous mixture is caused to flow through the catalyst with, the mixture containing 9.3% by volume ethylene, 6.0% by volume oxygen and, the remainder being nitrogen. The gaseous mixture further contains 0.8 ppm. dichloroethane.

The temperature is 275°C, the pressure is 11 kg/sq.cm. and the linear velocity of the gases amounts to 34 cm.second measured under the reaction conditions. As an average 315 g of ethylene oxide are obtained per liter of catalyst and per hour with, the selectivity referred to the converted ethylene amounting to 73%.

EXAMPLE 4

36 g of the catalyst of Example 2 are charged to a tubular reactor of AISI 316 steel, 9 mm in bore. The catalyst is exposed to a gaseous flow containing ethylene and oxygen, similar to that described in Example 3, the flow containing 1.5 ppm dichloroethane. The temperature is 275°C, the pressure is 11 kg/sq.cm. and the contact period is 2.7 seconds. As an average 195 g of ethylene oxide/liter catalyst/hour are obtained with, the selectivity referred to converted ethylene amounting to 72.5%.

What we claim is:

1. A method for preparing ethylene oxide by catalytic oxidation of ethylene with oxygen, which comprises contacting a gaseous stream containing ethylene and molecular oxygen with a catalyst obtained by the steps comprising:
   a. impregnating particles of a subdivided inert support with a heat-decomposable silver salt,
   b. drying said impregnated particles while heating to a maximum temperature not exceeding 160°C,
   c. flowing through the dried particles a gaseous stream consisting of superheated steam while raising the temperature to a selected value in the range of from 270°C to 350°C,
   d. progressively replacing in the gaseous stream and the steam by air over a period of at least 1 hour, while maintaining the temperature at a value substantially equal to said selected value, and
   e. maintaining the particles for at least 30 minutes under the gaseous stream consisting of air, while maintaining the temperature at a value substantially equal to said selected value.

2. The method of claim 1, wherein the temperature in steps (d) and (e) is maintained within ± 2°C of said selected value.

3. The method of claim 1, wherein step (d) is carried out over a period from 2 to 50 hours.

4. The method of claim 1, wherein step (e) is carried out for a period from 1 to 2 hours.

5. The method of claim 1, wherein steps (c), (d), and (e) are carried out with a velocity of the gaseous stream of from 0.1 to 5 meters/second.

6. The method of claim 4, wherein said velocity is about 0.5 meters/second.

7. The method of claim 1, wherein steps (c), (d) and (e) are carried out at a temperature of from 290° to 320°C.

8. The method of claim 1, wherein the support is selected from the group consisting of alumina, silicon carbide, magnesium oxide and mixtures thereof.

9. The method of claim 1, wherein the support consists of alpha-alumina having a specific surface area of from 0.01 to 1.0 sq.m/g, a porosity of 10–50% and an average pore diameter of from 20 to 180 microns.

10. The method of claim 1, wherein said support is in the form of beads from 4 to 9 mm in diameter.

11. The method of claim 1, wherein step (a) is carried out at a temperature from 60° to 115°C, the silver salt quantity being such as to provide 7 to 30% by weight silver metal with respect to the support.

12. The method of claim 11, wherein during the impregnation step a promoter selected from the group consisting of gold, palladium and platinum is added to the decomposable silver salt in a proportion of from 0.01 to 1.0% by weight with respect to the metallic silver.

13. The method of claim 11, wherein during the impregnation step a promoter consisting of a barium salt or a calcium salt is added to the decomposable silver salt, in an atomic proportion of from 0.1:100 to 5:100 of the barium salt or calcium salt, as barium or calcium, to metallic silver.

14. The method of claim 1, wherein the drying step (b) is carried out for a period of from 1 to 10 hours.

15. The method of claim 1, wherein the catalytic oxidation of ethylene is carried out at a temperature from 200° to 330°C, a pressure from 1 to 30 atmospheres and with a contact period from 1 to 10 seconds.

16. The method of claim 1, wherein said heat-decomposable silver salt is an organic silver salt.

17. The method of claim 16, wherein said organic silver salt is selected from the group consisting of the silver salt of lactic, citric, malic and isomalic acids.

* * * * *